United States Patent [19]

Chatterton

[11] E Patent Number: Re. 32,557

[45] Reissued Date of Patent: Dec. 8, 1987

[54] METHOD OF DETERMINING PREGNANEDIOL IN FEMALE URINE AND TEST DEVICE FOR USE THEREIN

[75] Inventor: Robert T. Chatterton, Chicago, Ill.

[73] Assignee: Northwestern University, Evanston, Ill.

[21] Appl. No.: 833,600

[22] Filed: Feb. 27, 1986

Related U.S. Patent Documents

Reissue of:

[64] Patent No.: 4,450,239
Issued: May 22, 1984
Appl. No.: 304,803
Filed: Sep. 23, 1981

[51] Int. Cl.[4] ..... G01N 33/53; G01N 33/552; G01N 33/544; B65D 69/00

[52] U.S. Cl. ..... 435/7; 422/56; 435/28; 435/805; 435/810; 436/510; 436/527; 436/528; 436/530; 436/531; 436/532; 436/537; 436/541; 436/542; 436/800; 436/810; 436/804; 436/814; 436/817

[58] Field of Search ..... 435/7, 28, 805, 810; 436/527, 528, 530, 531, 532, 537, 541, 542, 510, 800, 804, 810, 814, 817; 422/56

[56] References Cited

U.S. PATENT DOCUMENTS 4,123,510 10/1978 Barik et al. ..... 424/12

OTHER PUBLICATIONS

Chaudhri et al., J. Ster. Biochem., 13 (1980), 691–696.
DiPietro, Chem. Abstracts, 85 (1976), Abstract #89683a.
Manita et al., Chem. Abstracts, 88 (1978), Abstract #132867q.
Chatterton et al., Chem. Abstracts 96 (1982), Abstract #211087d.
Chaudri et al., J. Ster. Biochem. 16 (1982), 87–92.
Judge et al., Steroids, 31: 175–187, (1978).
Samarajeewa et al., J. Steroid Biochem., 11:1165–1171.
Collins et al., Acta Endocrinologica 90:336–348, (1979).

*Primary Examiner*—Christine M. Nucker
*Attorney, Agent, or Firm*—Tilton, Fallon, Lungmus & Chestnut

[57] ABSTRACT

A method is provided for determining the concentration of pregnanediol glucuronide (PG) in a woman's urine which is characterized by utilization of the reagent 20α-hydroxy-4-pregnen-3-one (20-α reagent) in a form in which it reacts with antibodies binding to PG. The method is adaptable to a visual color indication test which can be performed by the woman herself as well as by laboratory analysis. The method can be used to define the period in which conception can occur, to define a post-ovulation safe period in which conception is prevented, and as an early pregnancy indicator.

17 Claims, No Drawings

METHOD OF DETERMINING PREGNANEDIOL IN FEMALE URINE AND TEST DEVICE FOR USE THEREIN

Matter enclosed in heavy brackets [ ] appears in the original patent but forms no part of this reissue specification; matter printed in italics indicates the additions made by reissue.

*GRANT REFERENCE*

*The Government has rights in this invention pursuant to contract No. NO1-HO-9-2841.*

BACKGROUND AND PRIOR ART

The field of this invention relates to measurement of the concentration of the hormone pregnanediol in women's urine. In urine, this hormone occurs in the form of pregnanediol glucuronide (PG) and is detected in that form. The amount of PG in a woman's urine rises rapidly at the time of ovulation, and declines rapidly at the time of menstruation. However, if conception has occurred, the PG level remains high. Therefore, measurement of pregnanediol levels in urine is a potential usable procedure for either preventing or diagnosing pregnancy.

Although ovulation may be detected by characteristic in basal body temperature or in physical properties of cervical mucus, these methods are subject to variability from body functions unrelated to ovarian function and therefore not sufficiently reliable for detecting ovulation in many women.

Although pregnanediol is the major urinary product of progesterone, pregnanediol assays have not been widely utilized for assessment of luteal function. There are basically two reasons for this. First, earlier methods have required the collection of 24-hour urine specimens, an unreasonable request for even highly motivated patients when, to be most useful, collections should be made daily for at least 10 days during the middle of the menstrual cycle. Second, the assay procedure has been laborious, requiring usually two days for completion, and is subject to errors from several sources; the necessity for enzymatic or acid hydrolysis of the glucuronide moiety for colorimetry or gas chromatography is the most difficult and variable aspect of the assay.

It has been demonstrated that measurements of PG levels in overnight urine specimens correspond closely with 24-hour specimens. See Judge, et al, Steroids 31: 175–187 (1978). The reported tests were conducted on a laboratory basis by a gas chromatographic method.

Samarajeewa, et al have published a method for preparing antiserum specific for PG. J. Steroid Biochem. 11: 1165–1171 (1979). Pregnanediol in its free acid form was joined covalently to bovine serum albumin, and the antisera was prepared in rabbits. A calibration curve was prepared with radio-labelled PG, as part of the development of direct radioimmunoassay procedure for PG in women's urine. Specificity was established by showing that other steroids present in urine did not cross-react.

The antiserum prepared as described by Samarajeewa, et al, was used by Collins et al in radioimmunoassay procedure for measuring PG in overnight and 24-hour urine samples. Acta Endocrinologica 90: 336–348 (1979). The results confirmed the correlation previously observed by Judge et al. In the reported assay procedure, radio-labelled PG was employed as the test reagent for competing with the urine PG in binding to the antibodies of the immune serum. Thus, an expensive and relatively unstable reagent, pregnanediol glucuronide was required both for preparing the antiserum and as a radio-labelled test reagent, and the radioimmunoassay was carried out on a laboratory basis requiring special equipment. Heretofore, no one has provided the ovulation detection art with a simple, inexpensive and accurate procedure for determining levels of PG in urine which can be employed by women on a home-use basis.

SUMMARY OF INVENTION

This invention is based in part on the discovery that a commercially available relatively inexpensive steroid can be substituted for pregnanediol glucuronide in assay procedures using PG-antiserum. This steroid is 20α-hydroxy-4-pregnen-3-one (referred to herein as the 20-α reagent). Further, if desired, the antibodies binding to PG can be produced by using the 20-α reagent as the antigen. Even more importantly, however, the 20-α reagent can be used as the basis of a test kit for homeuse by women to determine PG in overnight urine samples, the level of PG in the urine being indicated by a visual color comparison. In one preferred embodiment, the 20-α reagent is immobilized on a solid adsorbent in the form of a fibrous strip, such as glass fiber paper, which can be dipped into the urine for reaction with the antibodies therein which have not bound to the PG of the urine. The amount of antibodies adsorbed on the strip can be indicated by having the antibodies labelled with a substance capable of providing a color reaction, such as a color compound like rhodamine, or an enzyme such as peroxidase which will react to produce a color. Alternatively, the amount of antibody protein bound to the test strip can be indicated by applying a protein staining dye such as Coomassie blue. Women are therefore provided with a simple, inexpensive and effective method for defining the time of ovulation. The woman may then use this information either to promote or prevent conception, or as a method for early self-diagnosis of pregnancy.

DETAILED DESCRIPTION

The method and indicator strip of the present invention utilize a 20-α reagent which comprises 20-αhydroxy-4-pregnen-3-one as the base reagent. The 20-α reagent as used in this invention is preferably in the form of a conjugated derivative which reacts readily with antibodies binding to pregnanediol glucuronide (PG). For example, the 20-α reagent can be conjugated through the C-3 of the steroid to a solid support material or to an antigenic protein. For example, a suitable coupling group is introduced at the C-3 position of the 20-α reagent. This does not modify the antigenic properties of the reagent, while adapting it for attachment to a glass fiber strip or other solid support, or to a suitable antigenic protein.

The other required reagent is the antiserum containing the antibodies binding to PG. This can be prepared by hyperimmunizing animals, such as rabbits, to a conjugate of PG and an antigenic protein, such as bovine thyroglobulin. For example, the procedure described by Samarajeewa, et al, J. Steroid Biochem. 11: 1165–1171 (1979), can be used. The 20-α reagent is conjugated to a suitable antigenic protein and used to prepare the antiserum. The antiserum obtained provides anti-PG antibodies that bind to the 20-α reagent either as the free steroid or as its C-3 derivatives.

In general, the method of this invention for determining the concentration of PG in a woman's urine is characterized by the steps of reacting a predetermined amount of anti-PG antibodies with a measured amount of the urine to leave a definite amount of unreacted antibodies for reaction with the 20-α reagent on the strip, or the antibodies are reacted with a measured amount of the urine which contains a quantity of a colored derivative of the 20-α reagent so that the reagent and the PG in the urine competitively react with anti-PG antibodies on the strip. In either case, after the reaction, either the amount of the reacted antibodies or the amount of unreacted 20-α reagent is determined. For example, this can be done by radiolabelling of the antibodies or the 20-α reagent. The radioimmunoassay may be conducted, in general, as described by Collins, et al, Acta Endocrinologica 90: 336–348 (1979), except that the radiolabelled 20-α reagent would be employed instead of radio-labelled PG. However, to achieve the full benefits of the present invention, it is preferred to employ a visual immunoassay procedure employing a color indicator.

In practicing the present invention, either a predetermined quantity of the antibodies or a predetermined quantity of the 20-α reagent can be immobilized on a color indicator support. For example, the support may comprise an adsorbent fibrous strip, such as that composed of porous glass beads or glass fiber paper. The antibodies may be attached to a solid surface without interfering with their binding capacity using the method described by Robbins and Schneerson, Methods in Enzymology 34: 703–731 (1974). Similarly, 20-α reagent may be bound to the glass without interfering with its reactivity with the antibodies by the method of Parikh et al, Methods in Enzymology 34: 670–688 (1974). General methods of conjugation to glass surfaces are described by Weetall and Filbert, Methods in Enzymology 34: 59–71 (1974).

In one preferred embodiment, a precise quantity of the 20-α reagent, provided with a coupling group at its C-3, is bound to a small test strip, such as a piece of glass fiber filter paper, and means are provided for dipping the entire strip in the urine. Such means may comprise tweezers, or the test strip may be attached to the end of a rod, the assembly providing a dipstick. Preferably, the antibodies to be added to the urine are labelled with a substance capable of providing a visual color indication. For example, the antibodies may be conjugated to a dye such as rhodamine. A suitable procedure for such conjugation is described in J. Immunol. Methods, 13: 305 (1976). After the reaction of the antibodies with the PG in the urine sample, the remaining unreacted antibodies are adsorbed by the 20-α reagent on the test strip. The intensity of the color will depend on the amount of the antibodies adsorbed. Further, additionally or alternatively, the antibodies after adsorption can be stained with a protein-staining dye such as Coomassie blue, bromophenol blue or tetrabromophenolphthalein ethyl ester.

One especially desirable procedure providing a high degree of color sensitivity is to conjugate the antibody to an enzyme which will produce a color reaction in a specific developing solution. For example, in one preferred procedure, the antibodies are conjugated to the enzyme peroxidase. This can be done by the method of Avrameas, Methods in Enzymology 44: 709–717 (1976). The unreacted portion of the antibodies are then adsorbed from the urine sample by the 20-α reagent on the test strip. The color is then developed by immersing the test strip in 0.05% of 3,3'-diaminobenzidine in pH 7.6 buffer. Hydrogen peroxide (2 drops of 3% solution) is added for color development. This procedure is also described in the article by Avrameas cited above.

In other procedures which could be employed, the 20-α reagent is conjugated to a color indicator dye such as rhodamine, and is used in the urine sample. A suitable procedure for such conjugation is described in J. Steroid Biochem., 13: 489–493 (1979). However, the sample of urine containing the color-indicator conjugated 20-α reagent is then contacted with the test strip for competitive adsorption of the PG and 20-α reagent. This procedure can provide a color indication of the amount of PG in the urine, it does not give as great a sensitivity or as clear a color discrimination as the procedures described above.

The technical basis for this invention and various embodiments thereof are further illustrated by the following examples.

EXAMPLE I

Antisera was produced in rabbits that were immunized by 3 intradermal injections 3 weeks apart with pregnanediol glucuronide that had been conjugated to bovine thyroglobulin via the mixed anhydride reaction. See Erlanger, et al, The Preparation of Steroid-Protein Conjugates to Elicit Antihormonal Antibodies, in Williams and Chase, Methods in Immunology and Immunochemistry, Vol. 1: Preparation of Antigens and Antibodies, New York, Academic Press, 1967; and Kellie, et al, Steroid Glucuronide-BSA Complexes as Antigens, The Radioimmunoassay of Steroid Conjugates, J. Steroid Biochem. 3: 275–288 (1972). The conjugate had been purified by dialysis and by precipitation from acetone. A 5 mg sample of the product was analyzed after it was hydrolyzed by heating in 0.75 N HCl in 66% (v/v) acetic acid at 100° C. for 15 minutes. The liberated steroid was extracted from the cooled, neutralized reaction mixture with ethyl acetate and was analyzed by gas chromatography. A molar ratio of steriod to protein of 157/1 was found. For each injection the conjugate was suspended in 1.0 ml of 0.9% NaCl and emulsified with an equal volume of Freund's incomplete adjuvant (the first injection in each animal was made with Freund's complete adjuvant). Rabbits received 2.5 mg of conjugate on each of the first 3 injections. Booster injections, also intradermal, were 0.25 mg. The titer of antisera was assessed by determination of the percent binding of $^3$H-pregnanediol in doubling dilutions of sera. The antiserum (0.2 ml) bound 50% of 15,000 dpm of $^3$H-pregnanediol at a serum dilution of approximately 1/5000.

EXAMPLE II

In order to test the specificity of pregnanediol glucuronide antiserum prepared as described in Example I, competition of several unlabelled steroids for $^3$H-pregnanediol was measured. Table A summarizes the activity of these steroids in terms of the inverse of the concentration of competitor divided by the inverse of the concentration of pregnanediol that is required for 50% decreases in binding of the labelled ligand. The antiserum was found to be highly specific for the 20-α reagent of this invention as well as for pregnanediol and its glucuronide, the reactivity of the 20-α reagent being of the same order as shown by the tabulated results.

TABLE A

| Specificity of Anti-pregnanediol Glucuronide Antiserum | |
|---|---|
| Steroid | % Competition |
| 5β-Pregnane-3α,20α-diol (pregnanediol) | 100 |
| Pregnanediol glucuronide | 133 |
| 20α-hydroxy-4-pregnen-3-one (20-α reagent) | 126 |
| 5β-Pregnane-3α,20α-diol | 0 |
| 5β-Pregnane-3α,17α,20α-triol | 0 |
| 5β-Pregnane-3α,20α-diol diacetate | 0 |
| Progesterone | 0 |
| Estradiol | 0 |
| Estriol | 0 |
| Androsterone | 0 |
| Cortisol | 0 |
| Corticosterone | 0 |

EXAMPLE III

The 20-α reagent can be bound to glass fiber paper after reacting the cleaned paper with 10% (v/v) 3-aminopropyltriethoxysilane in toluene. The free amino groups in this product can be cross-linked in 2.5% glutaraldehyde to polylysine (mol. wt. about 50,000). This provides a suitable support for covalently binding C-3 coupling derivatives of 20-α. For this purpose the 3-(0-carboxymethyl) oxime can be prepared in high yield by treatment of the 20-α steroid with aminooxyacetate in pyridine. This product can be conjugated directly, via the carbodiimide product promoted condensation, with the solid support (see Erlanger et al, cited in Example I), or a "bridge" such as p-aminobenzoic acid can be inserted between the steroid oxime and polylysine to decrease steric hindrance in the binding of antibody to the 20-α. See Weetall and Filbert, Methods In Enzymology, 34: 59–71 (1974). Using the carbodiimide procedure, 0.02 μmoles of steroid can be conjugated to 1 $cm^2$ of the solid support. This is more than 20 times the amount necessary to bind all of the antipregnanediol antibody (APD) that is required for the visual assay. An excess of binding capacity is needed to separate the APD that has not already bound pregnanediol glucuronide from the solution.

The glass fiber filter paper (or other solid surface) with the 20-α attached can be fastened to the inside surface of a tube in which the competition reaction takes place, or to a "dipstick" with an epoxy cement.

EXAMPLE IV

A preferred form the visual assay system employs 20-α bound to a solid support within a test tube. Sufficient lyophillized APD (purified IgG fraction) is added to the test tube to bind the amount of pregnanediol glucuronide typically found in 0.1 ml of urine from women six days after ovulation (0.0007 μmoles with an antibody valence of 2).

The person using the assay adds 0.1 ml of urine and an ampule containing 0.9 ml of buffer to the test tube that is already prepared as described above, and mixes the solution in the tube briefly. After 15 minutes, the solution is poured out, rinsed with water, and the indicator dye (Coomassie blue) is added. The color that develops within a few minutes is stable for several days, and can be compared with a color chart to determine the approximate level of pregnanediol glucuronide in urine.

The composition of the dye is that described by Bradford (Anal. Biochem. 72: 248, 1976). The darkest blue color develops when no pregnanediol glucuronide is present in the urine specimen, i.e., all of the APD is bound by the 20-α on the solid support. When the highest concentrations of pregnanediol glucuronide occur, e.g., after conception, the color will be light brown since very little APD will be available to bind to 20-α on the solid support and will be rinsed out of the tube. Intermediate concentrations of pregnanediol glucuronide in urine will give intermediate intensities of blue in the dye solution.

EXAMPLE V

In a procedure providing even greater reading sensitivity than that of Example IV, the antibodies are conjugated to peroxidase (Avrameas, Methods In Enzymology, 44: 709–717, 1976), and added to the urine in that form. The amount of antibody picked up and bound to a 20-α on the solid support in this case is measured by the color that develops on the surface of the solid support when the peroxidase enzyme that is conjugated to APD reacts with a substrate for a definite period of time. One preferred procedure is to add 0.5 mg of 3,3'-diaminobenzidine tetrahydrochloride in 1.0 ml of 0.1 M Tris-HCl buffer, pH 7.6. After adding a drop of 3% $H_2O_2$, the mixture is incubated for 5 min. at room temperature. The solution is poured out and the tube rinsed with water. Staining of the antibody on the solid support surface is proportional to the amount of antibody present. Quantification is done by the use of a color chart as with the procedure employing Coomassie blue.

EXAMPLE VI

The procedure for using the 20-α reagent in a radioimmunoassay requires that the tritiated form, [1,2-$^3$H(N)] 20α-hydroxy-4-pregnen-3-one, which is available from New England Nuclear Corp., 549 Albany Street, Boston, Mass, be substituted for the compound (pregnanediol glucuronide) to be measured. Antiserum (APD) prepared as described earlier is diluted until a concentration that binds approximately 70% of 20,000 dpm of tritiated 20-α (specific activity approximately 50 Ci/mmole) is obtained. This dilution of APD with the [$^3$H] 20-α is used to set up a standard curve in which either 20-α or pregnanediol glucuronide can be used as the steroid that is the competitor for [$^3$H] 20-α. If unlabeled 20-α is used as the competitor, a mathematical correction may have to be made for the difference in binding affinity of 20-α and pregnanediol glucuronide. Otherwise the procedures for radioimmunoassay are the standard methods.

Urine to be assayed is diluted 1/50, 1/100, and 1/500 with Buffer A (0.1 M sodium phosphate, 0.15 M sodium chloride, 0.015 M sodium azide, pH 7.0, containing 0.1% gelatin), and 0.1 ml aliquots of each dilution are added to assay tubes. Then 0.1 ml of the diluted antiserum (APD) containing 20,000 dpm of [$^3$H] 20-α is added to each sample. After incubation of the samples and standards for 2 hrs. at room temperature, the tubes are placed in a 4° C. cold room for ½ hour. Then, 0.2 ml of a suspension of dextran-coated charcoal (250 mg activated charcoal and 25 mg of dextran in 100 ml of Buffer A) is added to each tube. The samples are centrifuged to sediment the charcoal, and aliquots of the [$^3$H] 20-α bound to the diluted APD in solution are counted in a liquid scintillation counter.

The counting method and calculation of results by comparison of displacement of [$^3$H] 20-α from APD by samples and standards follow usual procedures.

I claim:

1. The method of determining the concentration of pregnanediol glucuronide (PG) in female urine comprising:

(a) adding to a measured sample of said urine a predetermined quantity of antibodies binding to PG, said antibodies being labeled with a substance capable of providing a visual color indication;

(b) contacting the reacted urine sample with a predetermined quantity of a 20-α reagent immobilized on a color indicator support, said reagent consisting essentially of 20α-hydroxy-4-pregnen-3-one, the unreacted labeled antibodies from said urine binding to said 20-α reagent on said support; and (c) determining from the intensity of color developed the concentration of PG in the urine sample.

2. The method of claim 1 in which said PG-binding antibodies are conjugated to a color indicator dye.

3. The method of claim 1 in which said PG-binding antibodies are conjugated to rhodamine.

4. The method of claim 1 in which the antibodies are conjugated to an enzyme capable of providing a color indication reaction.

5. The method of claim 1 in which said color indicator support provides glass surfaces for binding to said 20-α reagent.

6. The method of claim 1 in which said PG-binding antibodies are conjugated to a color indicator dye, and in which said color indicator support provides glass surfaces for binding to said 20-α reagent.

7. The method for claim 1 in which said antibodies after adsorption on said support are stained with a protein-staining dye for more intense color development.

8. The method of determining the concentration of pregnanediol glucuronide (PG) in a woman's urine, comprising:

(a) adding to a measured sample of said urine a predetermined quantity of a 20-α reagent, said reagent consisting essentially of 20α-hydroxy-4-pregnen-3-one and being labeled with a substance capable of providing a visual color indication;

(b) contacting the reacted urine with a predetermined quantity of antibodies binding to PG immobilized on a color indicator support, said labeled 20-α reagent and said PG reacting competitively with said antibodies; and (c) determining from the intensity of color developed the concentration of PG in the urine sample.

9. The method of claim 8 in which said 20α reagent is conjugated to an enzyme capable of providing a color indication reaction.

10. A test device for use in determining the concentration of pregnanediol glucuronide (PG) in a sample of female urine, comprising a color indicator support having immobilized thereon a known quantity of a 20-α reagent consisting essentially of 20α-hydroxy-4-pregnen-3-one.

11. The test device of claim 10 in which said support provides glass surfaces for binding to said 20-α reagent.

12. A test strip for use in determining the concentration of pregnanediol glucuronide in a sample of a woman's urine, comprising an adsorbent fibrous strip having immobilized thereon a known quantity of a 20-α reagent consisting essentially of 20α-hydroxy-4-pregnen-3-one.

13. The test strip of claim 12 in which said strip is composed of a glass fiber paper.

*14. The method of determining the concentration of pregnanediol glucuronide (PG) in female urine, comprising:*

*(a) adding to a measured sample of said urine a predetermined quantity of antibodies binding to PG for reacting said antibodies with the amount of PG in the urine, said antibodies being in excess of the amount of PG to leave unreacted antibodies;*

*(b) contacting the antibody-containing sample with a quantity of a 20-α reagent immobilized on a support for reacting the antibodies which have not reacted with said PG with said 20-α reagent on said support, said 20-α reagent consisting essentially of a 20-α-hydroxy-4-pregnen-3-one, the said quantity of 20-α reagent being at least sufficient to bind the PG-unreacted antibodies;*

*(c) separating the residual urine sample from said support with said PG-unreacted antibodies bound thereto; and, thereafter,*

*(d) determining the amount of PG-unreacted antibodies thus separated from the urine sample as a measure of the PG concentration in the urine sample by (i) a color change reaction indicating separated antibody quantity, or (ii) by means of an enzyme associated with said separated antibodies which enzyme is capable of providing a color reaction indicating antibody quantity, or (iii) by means of a protein-staining dye which dye is capable of providing a color reaction indicating antibody quantity, or (iv) by means of a radiolabel associated with said separated antibodies which radiolabel is capable of providing an indication of antibody quantity.*

*15. The method of claim 14 in which said support provides glass surfaces to which said 20-α reagent is bound.*

*16. A test device for use in determining the concentration of pregnanediol glucuronide (PG) in a sample of female urine comprising a support having immobilized thereon a quantity of a 20-α reagent consisting essentially of a 20-α hydroxy-4-pregnen-3-one, said immobilized 20-α reagent being capable of binding to antibodies binding to PG.*

*17. The test device of claim 16 in which said support provides glass surfaces to which said 20-α reagent is bound.*

* * * * *